United States Patent
Lewis et al.

(10) Patent No.: US 7,011,619 B1
(45) Date of Patent: Mar. 14, 2006

(54) APPARATUS AND METHODS FOR RADIOTHERAPY

(75) Inventors: Dewi M. Lewis, Prestwood (GB); Lucinda A. Dollimore, Gerrards Cross (GB); Nigel Powell, Reading (GB); Gregory L. McIntire, West Chester, PA (US); Evan Gustow, Villanova, PA (US); Robert A. Snow, West Chester, PA (US)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 09/763,006

(22) PCT Filed: Aug. 13, 1999

(86) PCT No.: PCT/GB99/02687

§ 371 (c)(1),
(2), (4) Date: Mar. 30, 2001

(87) PCT Pub. No.: WO00/09212

PCT Pub. Date: Feb. 24, 2000

Related U.S. Application Data (60) Provisional application No. 60/138,874, filed on Jun. 11, 1999, provisional application No. 60/098,721, filed on Sep. 1, 1998.

(30) Foreign Application Priority Data

| Aug. 13, 1998 | (GB) | .................................... 9817674 |
| Jul. 5, 1999 | (GB) | .................................... 9915718 |

(51) Int. Cl.
*A61N 5/00* (2006.01)
(52) U.S. Cl. ........................ 600/3; 600/1; 600/7; 600/8
(58) Field of Classification Search ................ 600/1–8
See application file for complete search history.

(56) References Cited

U.S. PATENT DOCUMENTS

| 3,351,049 A | | 11/1967 | Lawrence |
| 4,323,055 A | * | 4/1982 | Kubiatowicz .............. 424/1.11 |
| 4,696,808 A | | 9/1987 | Barber et al. |
| 4,994,013 A | | 2/1991 | Suthanthiran et al. |
| 5,342,283 A | | 8/1994 | Good |
| 5,405,309 A | * | 4/1995 | Carden, Jr. .................... 600/3 |
| 6,030,333 A | * | 2/2000 | Sioshansi et al. .............. 600/3 |
| 6,183,409 B1 | * | 2/2001 | Armini .......................... 600/3 |
| 6,455,024 B1 | * | 9/2002 | Glajch et al. .................. 600/3 |
| 6,458,069 B1 | * | 10/2002 | Tam et al. ...................... 600/3 |

FOREIGN PATENT DOCUMENTS

| EP | 0037678 | 10/1981 |
| FR | 2717610 | 9/1995 |

* cited by examiner

OTHER PUBLICATIONS

Int'l Search Report PCT/GB99/02687 dated Feb. 2000.

*Primary Examiner*—Steven J. Ganey
(74) *Attorney, Agent, or Firm*—Robert F. Chisholm (57) ABSTRACT

The invention provides the use of a radiation source which is a low energy X-ray emitter, e.g. with an energy of emission of the principal photon in the range of 20 to 100 keV, preferably 20 to 40 keV and with a half life of 10 to 100 days, preferably 15 to 70 days, for the treatment of restenosis. Suitable radioisotopes include palladium-103, dysprosium-159, samarium-145, cadmium-109, ytterbium-169 and preferably iodine-125. High activity radioactive bodies and sources comprising such radioisotopes, and methods for the manufacture of such sources, are also disclosed.

25 Claims, 4 Drawing Sheets

APPARATUS AND METHODS FOR RADIOTHERAPY

This application claims the benefit of Provisional Application Nos. 60/098,721, filed Sep. 1, 1998 and 60/138,874, filed Jun. 11, 1999.

This invention relates to radiotherapy. More particularly, it relates to a radioactive source, to its use in therapy and to methods for its manufacture.

Brachytherapy is a general term covering medical treatment which involves placement of a radioactive source near a diseased tissue and may involve the temporary or permanent implantation or insertion of a radioactive source into the body of a patient. The radioactive source is thereby located in proximity to the area of the body which is being treated. This has the advantage that a high dose of radiation may be delivered to the treatment site with relatively low dosages of radiation to surrounding or intervening healthy tissue.

Brachytherapy has been proposed for use in the treatment of a variety of conditions, including arthritis and cancer, for example breast, brain, liver and ovarian cancer and especially prostate cancer in men (see for example J. C. Blasko et al., *The Urological Clinics of North America*, 23, 633–650 (1996), and H. Ragde et al., *Cancer*, 80, 442–453 (1997)). Prostate cancer is the most common form of malignancy in men in the USA, with more than 44,000 deaths in 1995 alone. Treatment may involve the temporary implantation of a radioactive source for a calculated period, followed by its removal. Alternatively, the radioactive source may be permanently implanted in the patient and left to decay to an inert state over a predictable time. The use of temporary or permanent implantation depends on the isotope selected and the duration and intensity of treatment required.

Permanent implants for prostate treatment comprise radioisotopes with relatively short half lives and lower energies relative to temporary sources. Examples of permanently implantable sources include iodine-125 or palladium-103 as the radioisotope. The radioisotope is generally encapsulated in a metal casing, preferably a titanium or stainless steel casing, to form a "seed" which is then implanted. Temporary implants for the treatment of prostate cancer may involve iridium-192 as the radioisotope.

Recently, brachytherapy has also been proposed for the treatment of restenosis (for reviews see R. Waksman, *Vascular Radiotherapy Monitor*, 1998, 1, 10–18, and *MedPro Month*, January 1998, pages 26–32). Restenosis is a renarrowing of the blood vessels after initial treatment of coronary artery disease, peripheral artery disease or any arterial component of the vascular system.

Coronary artery disease is a condition resulting from the narrowing or blockage of the coronary arteries, known as stenosis, which can be due to many factors including the formation of atherosclerotic plaques within the arteries. Such blockages or narrowing may be treated by mechanical removal of the plaque, by laser treatment to vaporise the plaque or by insertion of stents to hold the artery open. One of the most common forms of treatment is percutaneous transluminal coronary angioplasty (PTCA)—also known as balloon angioplasty. At present, over half a million PTCA procedures are performed annually in the USA alone. In PTCA, a catheter having an inflatable balloon at its distal end is inserted into the coronary artery and positioned at the site of the blockage. The balloon is then inflated which leads to flattening of the plaque against the artery wall and stretching of the artery wall, resulting in enlargement of the intraluminal passage way and hence increased blood flow.

PTCA and PTA has a high initial success rate but 30–50% of patients present themselves with stenotic recurrence of the disease within 6 months. This recurrence is known as restenosis, and is a renarrowing of the blood vessels following the initial treatment. It is believed that restenosis is due, at least in part, to a natural healing response to damage caused to the artery by the original PTCA procedure (i.e. by the inflation of the angioplasty balloon). Such damage may be due to stripping of the endothelium, cracking, splitting and/or disruption of the plaque or of the intima, or injury to the media or to the vessel smooth muscle, or stretching or tearing of the adventitia (the outer surface of the artery).

One treatment for restenosis which has been proposed is the use of intraluminal radiation therapy (for a review see R. Waksman, Vascular Radiotherapy Monitor, 1998, 1, 10–18). In such treatment, a radioactive source is positioned inside the artery at the site of restenosis, thus leading to irradiation of the site. It has been postulated that irradiation inhibits the growth of new cells and hence slows down the natural healing processes which can lead to restenosis (see e.g. MedPro Month, January 1998, pages 26–32).

Various radioisotopes have been proposed for use in the treatment of restenosis. Delivery of the radioactive source to the treatment site may be achieved using conventional catheter procedures to deliver radioactive sources or by permanent implantation of radioactive stents. Alternatively, the use of a solution of a radioactive isotope inside a catheter balloon has also been proposed. The use of radioactive liquids increases the risks involved with the procedure due to the possibility of leakage of the radioactive material either inside the patient or when the catheter is being transported, stored or set up.

Both gamma and beta emitters have been considered for use as the radiation source. High energy gamma emitters such as iridium-192 create a radiation field for a considerable distance away from the source. Their use entails the provision of shielding to protect both the patient and the medical staff supervising the procedure. In many cases, the medical personnel must actually leave the room whilst the patient is undergoing treatment with the radioactive source, to minimize the radiation dose burden to medical personnel. As the irradiation can take 15–45 minutes, a catheterised (and often apprehensive) patient may have to be left alone for a significant period of time.

The use of beta emitters such as strontium-90, yttrium-90, phosphorus-32, rhenium-186 and rhenium-188 has also been proposed. Beta emitters do not require the extensive shielding for personnel protection that is necessary with gamma emitters, since the radiation field from beta emitters falls off very quickly as a function of the distance from the source. However, this rapid fall off in the radiation field with distance from the source affects the capability of beta emitters to provide an adequate radiotherapeutic effect to the whole thickness of the coronary artery wall. It is possible that the arterial wall may be too thick and that hence the radiation field may fall below a level where there is sufficient therapeutic benefit. Additionally, the arterial wall may be eccentric and hence the distances involved may again be too great for sufficient radiation penetration. In diseased coronary arteries, thick lipid deposits or dense calcified plaques may be present which may also attenuate the radiation field to an insufficient level. Often metallic intraluminal stents may be present around the diseased site and their presence may also prevent adequate radiotherapy dosimetry from beta emitters.

There is therefore still a need for a radioactive source which produces a radiation dose field suitable for the treatment of restenosis but which does not suffer from the dosimetric deficiencies of a beta emitter nor the radiological hazards of an energetic gamma emitter such as iridium-192, and which also does not involve the use of any radioactive liquids.

The present invention therefore discloses the use of a radiation source which is a low energy X-ray emitter, e.g. with an energy of emission of the principal photon in the range of 20 to 100 keV, preferably 20 to 40 keV and with a half life of 10 to 100 days, preferably 15 to 70 days, for the treatment of restenosis. Suitable radioisotopes include iodine-125, palladium-103, dysprosium-159, samarium-145, cadmium-109 and ytterbium-169. Iodine-125, which has a half life of 59.6 days and emits low energy X-ray radiation with an average energy of 28.5 keV, is particularly appropriate. Palladium-103 is also appropriate.

As one aspect of the invention there is therefore provided a radioactive body suitable for use in brachytherapy, and preferably capable of insertion into a mammalian blood vessel to combat restenosis, preferably a sealed source, containing a low energy X-ray emitter (for example iodine-125, palladium-103, dysprosium-159, samarium-145, cadmium-109 and ytterbium-169, preferably palladium-103 or iodine-125 and most preferably iodine-125). The activity of the radioactive body (measured externally) is in the range of about 2 to about 740 GBq (about 56 mCi to about 20 Ci), preferably about 37 to about 370 GBq (about 1 Ci to about 10 Ci), more preferably about 74 to about 185 GBq (about 2 to about 5 Ci). The radioactive body may comprise one or more radioactive sources, for example seeds. The individual radioactive sources may have an activity in the range of about 3700 to about 37,000 MBq (about 100 to about 1000 mCi), preferably about 7400 to about 18,500 MBq (about 200 to about 500 mCi) and more preferably about 9250 to about 14,800 MBq (about 250 to about 400 mCi). When the X-ray emitter is iodine-125, a preferred range is about 7400 to about 44,000 MBq (200–1200 mCi), preferably about 11,100 to about 37,000 MBq (300 to 1000 mCi), more preferably about 14,800 to about 22,200 MBq (400 to 600 mCi).

The values for the activity ranges given herein are the appropriate values when the radionuclide is iodine-125, with the proviso that when the radionuclide is iodine-125 itself, the lower end of the activity range of the radioactive body is 3700 MBq (100 mCi), and preferably at least 7400 MBq (200 mCi). Equivalent activity ranges appropriate for other radionuclides are also within the scope of the invention. The activity ranges depend on the radionuclide used, as the total radiation dose delivered by a radioactive body depends upon the energy of the emissions of the particular radionuclide in question. Such activity ranges can readily be calculated by a skilled man to give an equivalent radiation field as if a radioactive body containing iodine-125 in the above-mentioned activity ranges was used.

By radioactive body is meant an object that contains a radiation emitter, for example one or more sealed containers (a "sealed source") containing the emitter within a sealed chamber but permitting radiation to exit through the container/chamber walls. Implantable radioactive bodies in the form of iodine-125 or palladium-103 containing small sealed metal cylinders are known and are referred to as "seeds". Such seeds are known in the art for use as permanent implants in brachytherapy (see for example U.S. Pat. No. 3,351,049 and U.S. Pat. No. 4,323,055); however the source strength of the known seeds is not of sufficient intensity for use in the treatment of restenosis. Currently available iodine-125 seeds for human implantation have source strengths in the range of 6.66–1480 MBq (0.18–40 mCi). Such seeds cannot deliver a sufficient radiation dose for the treatment of restenosis within an acceptable time scale. It is clearly undesirable to keep a patient catheterised for long periods, so the radiation source should be of sufficient strength that a therapeutically useful (but in other respects harmless) radiation dose is delivered within a reasonable time.

For the treatment of restenosis, the treatment time is preferably such that the required radiation dose is administered in under 1 hour, preferably within 3 to 45 minutes and most preferably within 5 to 30 minutes. The treatment time in any particular case is calculated to give the required dose to the patient and will be inversely proportional to the level of activity of the radioactive source. It will also depend on the energy of the radioactive emissions and on the half life of the radioisotope used.

In the treatment of restenosis of arteries, the dose to the inner blood vessel wall should preferably be about 15 to 40 Grays, more preferably about 25 Grays, whilst the radiation dose to the outer surface of the blood vessel should preferably be no greater than 30 Grays, more preferably no greater than 15 Grays and most preferably no greater than 8 Grays.

Preferably, the radiation dose to the inner blood vessel wall should be chosen to be a maximum dose level which is consistent with not over-irradiating matter leading to consequential long-term structural damage and also not leading to excessive doses to unconnected healthy tissue, the patient's body or to the attending clinical staff. The radiation dose to the outer surface of the blood vessel should be at a level which does not impair healthy tissue function.

The radioactive body of the invention may comprise one or more radioactive sources of a suitable shape.

The radioactive source preferably comprises a radioisotope and one or more supports, which can be e.g. a bead, rod, wire, filament etc. The support is preferably of a suitable size and dimensions to fit inside a container which is formed into a sealed radioactive source. For example, the support may be rod-like or substantially spherical. However, the support may be any size or shape suitable for irradiating the lumen of occluded blood vessels for the prevention of restenosis, and the size and shape of the container may be chosen depending on the dimensions of the support.

Such supports advantageously have a cross sectional area and configuration such that adjacent supports do not overlap along the length of an elongate radioactive body to produce a substantially non-uniform radiation density at that site.

The support may be made of ion exchange or other polymer resin, graphite, ceramic, zeolite or other, preferably porous, material or it may be made completely of metal, or may comprise a layer of metal plated onto a suitable substrate. Suitable substrate materials include a second metal such as gold, copper or iron, or solid plastics such as polypropylene, polystyrene, polyurethane, polyvinyl alcohol, polycarbonate, Teflon™, nylon, delrin and Kevlar™. Such solid plastics are also suitable support materials. Other suitable substrates or support materials include carbon, alumina, titanium dioxide, zeolites or ceramics. Suitable plating methods are known in the art and include chemical deposition, sputtering, ion plating techniques, electrodeless plating and electrodeposition. The support material should be sufficiently stable to radiation such that a source comprising the support may be incorporated into a radioactive body for use in brachytherapy.

Suitable polymers for use as a support include those listed below with trade names and commercial sources in brackets:

Polyurethane (Texin, Desmopan, Estane from Bayer Corp and B F Goodrich)

Polypropylene (Surgilene, Prolene from Ethicon, American Cyanamid)

Polyethylene terephthalate, PET (Impet, Petra Rynite, Estar from Allied, Hoechst, Celanese, Du Pont, Eastman)

Polyethylene oxide blends (Noryl, Prevex from GE)

Polyphenylsulphone, PPSU (Radel R from Amoco)

Polysulphone, PSU (Udel, Ultrason S from Amoco, BASF)

Polyether sulphone, PES (Radel A, Ultrason E from Amoco, BASF)

Polyphenylene sulphide, PPS (Fortron, Ryton, Supec from Hoechst, Celansess, Phillips, GE)

Phenyletheretherketone, PEEK (Kadel, Victrex from Amoco, Victrex)

Polyetherimide, PEI (Ultem from GE)

Silicone (Silastic from Dow Corning)

Liquid Crystal Polymer, LCP (Vectra from Hoechst, Celanese)

Polyglycaprone 25 (Moncryl, Ethicon)

Polyglactin 910 (Vicryl, Ethicon)

Polydioanone (PDS II, Ethicon)

Nylon

Polyphenylene oxide blends.

Preferred radiation-resistant polymers for the support or catheter insert tip are phenyletheretherketone (PEEK), nylon or polyurethanes, with PEEK being especially preferred.

When the support is or comprises a metal, suitable metals for the support include silver, copper, palladium, thallium, gold, lead and platinum.

Preferred materials for the support are ion exchange resins, metals or low atomic number materials such as graphite. When the radioisotope is $^{125}$I, a preferred metal for the support is silver or a preferred non-metal is carbon.

The chemical form of the radioisotope on the support is preferably involatile. When the radioisotope is a radiometal, this could be the radiometal itself or an insoluble salt of the radioisotope. When the radioisotope is $^{125}$I, the radioiodine is preferably present as an involatile, insoluble metal iodide. The metal support material is thus a metal which forms an insoluble iodide salt.

One or more supports plus radioisotope are preferably sealed inside a container, for example a substantially cylindrical tubular container made of metal or some other suitable material. The container material should be corrosion resistant, compatible with body fluids and non-toxic and should not unduly absorb the low energy X-ray radiation emitted from the radioisotope. Suitable containers include those made of low atomic numbered metals such as titanium or stainless steel. Higher atomic number metals such as gold or platinum result in too much radiation attenuation to be useful per se. However, they may be useful as a plating over certain low atomic number metals such as beryllium which would otherwise be too toxic if used without an outer coating. Titanium, titanium alloys or stainless steel are preferred metals for use in the container. The container is preferably completely sealed so there is no danger of leakage.

Some radiation may be absorbed by the support and/or the container. The amount of radioisotope required to provide radioactive source(s) and in turn a radioactive body of a given activity will depend in part on the amount of such attenuation. The amount of attenuation in any given case can be readily determined by a skilled person, for example by trial and error experimentation or by calculation.

The radioactive body should be of an overall size and dimensions suitable for its intended use. For example, the overall dimensions of each radioactive body should preferably be such that it can be delivered to the treatment site using conventional techniques, for example it can be loaded inside a conventional catheter for delivery to the site of restenosis. Seeds for use in the treatment of prostate cancer, for example, are typically substantially cylindrical in shape and approximately 4.5 mm long with a diameter of approximately 0.8 mm, such that they may be delivered to the treatment site using a hypodermic needle. For use in the treatment of restenosis, a single body should be of suitable dimensions to be inserted inside a coronary artery, for example have a length of about 10 mm and a diameter of about 1 mm, preferably a length of about 5 mm and a diameter of about 0.8 mm, and most preferably a length of about 3 mm and a diameter of about 0.6 mm. Radioactive bodies for use in the treatment of restenosis are typically delivered to the treatment site using conventional catheter methodology.

For elongate radioactive bodies, the radiation intensity (activity) (measured externally) is preferably in the range about 0.5 to 74 GBq/cm (15 mCi/cm to 2 Ci/cm), especially 0.5 to 40.7 GBq/cm (15 mCi/cm to 1.1 Ci/cm) and more especially 3.7 to 29.6 GBq (100 to 800 mCi/cm), with the cm dimension referring to the overall length of the body. Where a plurality of radioactive bodies are to be located at a treatment site, e.g. a substantially linear array especially a train of such bodies, the average radiation intensity over the length of the array or train is preferably 0.5 to 74 GBq/cm (15 mCi/cm to 2 Ci/cm), especially 0.5 to 40.7 GBq/cm (15 mCi/cm to 1.1 Ci/cm) and more especially 3.7 to 29.6 GBq (100 to 800 mCi/cm).

Since the radioactive bodies are preferably of dimensions similar to or comparable with those of the known radioactive seeds, such bodies will be referred to hereinafter as seeds. Alternative configurations however may of course be used.

If the seeds comprise supports in the form of beads, typically each individual seed will contain from 3 to 5, usually 4 beads, preferably separated by spacers. The beads are preferably spaced such that a cylindrically substantially uniform radiation field around the seed will result. One or more of the spacers is preferably radiopaque, for example made of silver, lead, platinum, iridium or a mixture of these metals, to aid placement of the seed at the treatment site. Radiopaque spacers can be visible using X-ray imaging techniques, which enables seeds comprising such spacers to be positioned more accurately within the patient's body.

Preferably, the overall radiation field around the seeds is as uniform as possible and the radiation profile is as flat as possible so that localised "hot spots" or "cold spots" do not occur inside the patient. If the radiation source is in the form of support-containing seeds, the supports are preferably arranged such that the radiation field is substantially uniform and the radiation profile is flat. The ends of a seed container often have thicker walls than the sides due to the manufacturing process which involves inserting the seeds inside a metal container and sealing, e.g. welding shut, the ends of the container. These so-called end effects can result in a non-uniform radiation field and accordingly in one preferred arrangement the radioactive supports, for example beads, within the seed are selected such that more active supports are placed at the ends and less active ones in the centre or vice versa. This is a novel arrangement and forms a further aspect of the invention.

As a further aspect of the invention there is therefore provided an elongate radioactive seed containing a plurality of radioactive supports, preferably beads, of different activities such that there is a substantially cylindrically uniform radiation field around the seed and over a predetermined length.

As mentioned above, for a seed containing a plurality of supports, the end supports in an individual seed may be chosen so that they are of higher activity than the central supports in order to obtain a more uniform field than is obtained if all the supports within the seed have substantially the same activity. Similarly, when the radioactive body comprises a train or linear array of e.g. four radioactive seeds, the central two seeds may be provided with lower activity than the end two seeds, to achieve an equivalent effect for the radiation dose field from the whole radioactive body. For iodine-125 carrying supports, for example, a suitable ratio of activities is typically 10:8:8:10. For palladium-103, a suitable activity ratio is typically 10:9:9:10. A skilled man will be able to readily calculate or determine by suitable trial experiments the desired activity ratio for any particular arrangement. Such an arrangement also has the advantage that there is a lower risk of over-irradiation or under-irradiation of sections of the lumen when a train of such seeds negotiates a curved portion of the lumen than there is when all the seeds or supports have substantially the same activity.

A catheter will typically be loaded with a number of seeds, for example 2 to 20 (e.g. 3, 5, 7, 9, 11, 13 or 15) seeds in a substantially linear array or train, optionally separated by spacers or articulators to help increase the flexibility of the array. Preferably the articulators and/or spacers are radiopaque so they may be visible by X-ray and may aid in the positioning of the seeds within a patient. The articulators and spacers should also be made from materials which are resistant to radiation. Suitable shapes for articulators or spacers include cylinders (e.g 0.5×0.4 mm), spheres (e.g. 0.8 mm diameter) or rings (e.g 0.6 mm inner diameter and 0.7 mm outer diameter). A preferred spacer comprises six rods or bars of equal length radiating in mutually orthogonal directions from a single point. Suitable materials for use in the spacers and articulators include metals such as gold, tantalum, platinum or iridium and plastics such as polyethylene.

For example, a linear array of seeds may be encapsulated in a polymer material in the form of a catheter insert tip, which may then be attached to a metallic thrust wire for insertion into another catheter. Alternatively, a linear array of seeds may be positioned at the distal end of a catheter or other flexible linear probe before insertion of the catheter or probe into the artery.

If conventional methods of manufacturing low activity iodine-125 ion-exchange resin beads (see for example U.S. Pat. No. 3,351,049) are adapted to the production of higher activity beads, then problems may arise with a wide spread of activity levels across the beads. Such variability is undesirable from a manufacturing standpoint as it would necessitate quality control accept/reject testing which is undesirable as it entails the further handling of highly radioactive materials and potential waste. If no quality control was undertaken, radioactive bodies with non-uniform radiation fields would be likely to result due to the non-uniform activity of the component beads.

As a further aspect of the invention there is provided a method for the manufacture of radioactive beads, said method comprising the steps of:

a) preparing a batch of suitable ion exchange resin beads by soaking the beads in a solution containing an anion or cation replaceable by the desired radioisotope, and then washing the beads with water until the wash water is free of such anions or cations;

b) drying the batch and placing a bead thereof in each of one or more individual reaction wells;

c) placing an equal volume of a solution comprising anions or cations of the desired radioisotope in each reaction well;

d) leaving each bead in the radioisotope solution for a predetermined length of time so that the radioisotope is absorbed by each bead; and e) removing the supernatant, washing and drying the beads.

The above method may be applied to a batch comprising 1 to about 1000 or more beads, preferably from about 2 to about 200 beads.

The above method is a reliable and reproducible method for the manufacture of a batch of radioactive beads, for example a batch of high activity beads containing iodine-125 as the radioactive source. The above method can readily be adapted to the reproducible loading of high levels of radioisotope on to a range of different support materials or differently shaped supports. One or more of such beads will desirably be suitable for use in brachytherapy techniques, such as in the treatment of restenosis. Seeds comprising such beads may have a source strength in the range of 2 to 740 GBq (56 mCi to 20 Ci) per seed once the seeds are loaded and sealed. Individual beads, before loading into seed casings (or after unloading from such casings) will conveniently have an activity of 3.7 to 37 GBq (0.1 to 1 Ci), preferably 11 to 26 GBq (300 mCi to 700 mCi). Other convenient activity ranges for the individual beads are 518 to 30,525 MBq (14 to 825 mCi), preferably 925 to 9250 MBq (25 to 250 mCi) and more preferably 1850 to 4625 MBq (50 to 125 mCi). Such a bead comprises a yet further aspect of the invention.

Through the choice of suitable resins, solutions and radionuclides, the method may be used for the manufacture of beads comprising, for example, radioisotopes of iodine (e.g $^{125}$I and $^{131}$I), strontium (e.g. $^{89}$Sr), phosphorus (e.g. $^{32}$P and $^{33}$P), yttrium (e.g. $^{90}$Y), indium (e.g. $^{114m}$In), rhenium (e.g. $^{186}$Re and $^{188}$Re), technetium (e.g. $^{99}$Tc, $^{99m}$Tc), palladium (e.g. $^{103}$Pd), dysprosium (e.g $^{159}$Dy), samarium (e.g. $^{145}$Sm), cadmium (e.g. $^{109}$Cd) and ytterbium (e.g.$^{169}$Yb).

The above method may also be readily automated.

Suitable ion exchange resins include those known in the art for the preparation of radioactive beads. For example, for iodine-125 beads a suitable ion exchange resin is Bio Rad AG1-X8 anion exchange resin, whilst for strontium beads, a suitable ion exchange resin is AG50W-X8 cation exchange resin. Zeolites may also be used in place of the ion exchange resins. Each bead is preferably approximately 500–600 $\mu$m in diameter. The material(s) of which the beads are comprised should be resistant to the radiation emitted by the radioisotope(s).

In step a), suitable soaking solutions are known in the art. For example, if $^{125}$I$^-$ is the desired radioisotope, an NaCl solution is a suitable soaking solution, as chloride is an anion replaceable by iodide.

In step c), a solution of any salt of the desired radioisotope which is sufficiently soluble may be used as the source of the radionuclide. Suitable sources are well known in the art. A preferred solution when the radioisotope is $^{125}$I$^-$ is a solution of Na$^{125}$I.

In step d), the length of time for which the beads are left in the solution depends in part on the concentration of the solution and also on the desired activity of the product beads. The preferred-length of time can be calculated or can be determined via routine initial trial experiments. For example, the disappearance of radioactivity from the supernatant solution can be readily monitored. Preferably, the bead should be left in solution until about 95% of the radioactivity of the supernatant solution has been absorbed.

During one or more of steps b) to e) a desiccant polymer such as dihydroxypropylcellulose may also advantageously be present to absorb water.

The reaction wells may be individual wells in a reaction well plate comprising an array of uniformly sized reaction wells. This has the advantage that the method may be readily automated using conventional reaction automation apparatus.

In an alternative process to produce radioactive bodies according to the invention, radioactive iodine can be attached to a metal surface by first forming an insoluble salt on the surface, e.g. chloriding or bromiding the metal to form a layer of insoluble metal chloride or metal bromide, and then replacing some of the anions in the insoluble salt with radioactive iodide ions by simple ion exchange, as disclosed in U.S. Pat. No. 4,323,055 which is incorporated by reference. In order for the ion exchange step to work, the initially formed insoluble salt should be less insoluble in the reaction medium than is the metal iodide.

A layer of metal chloride or metal bromide may be formed on the surface of the support using conventional chemical or electroplating processes. For example, a support may be placed in an aqueous solution of an oxidising agent containing chloride or bromide anions. Suitable oxidising agents include sodium chlorite ($NaClO_2$), sodium chlorate ($NaClO_3$), sodium chromate ($NaCrO_4$), potassium dichromate ($K_2Cr_2O_7$) and potassium permanganate ($KMnO_4$).

As some metal halides and in particular silver halides are light-sensitive, preferably the process is carried out under conditions wherein the exposure of the coated substrates to visible blue or UV light is minimized prior to encapsulation of the source within a container. For example, the process may be carried out under "safe" lights, for example red or yellow lights. However, in some cases it may be possible to carry out the method of the invention under normal room (i.e. fluorescent) light without undue adverse effects. Whether or not normal room light is suitable may be readily determined using routine trial and error experimentation.

The insoluble salt-coated supports, for example the chlorided or bromided supports, are exposed to a source of radioactive iodide ions, for example an aqueous solution of a soluble radioactive iodide salt such as sodium iodide, for a sufficient period of time for substantially all of the radioactive iodide to exchange with some of the anions, for example bromide or chloride ions, on the support surface. The amount of insoluble salt present before the ion exchange should be such that substantially all of the radioactive iodide ions can exchange with the anions to form silver iodide. Optionally, excess insoluble salt may be present, such that some remains after the ion exchange.

The level of radioactivity of a source prepared using the method of the invention will depend in part on the amount of radioactive iodide ions used in the method. Substantially all of the iodide ions should exchange for the anions in the insoluble salt and so be present in the final product.

It has now been found that individual high activity sources made using the bulk processes disclosed in U.S. Pat. No. 4,323,055 display a very wide spread of iodine-125 uptake, leading to only a few of the sources being suitable. However, it has surprisingly been found that individual high activity sources may be more reliably made using this process provided that each support is processed in a small batch, preferably individually. Small batches of, for example, 1 to 10 supports, preferably 1 to 5 supports, may be suitable, although processing of a batch comprising a single support is preferred.

As a further feature of the invention there is therefore provided a method for immobilising radioactive iodide ions on the surface of a metal or metal coated support, the method comprising forming a layer of an insoluble metal salt on the surface of the support, and replacing anions in the insoluble salt with radioactive iodide ions by ion exchange, wherein the ion exchange is carried out on each support individually. Preferably the metal is silver, especially in the form of a silver wire, and the insoluble salt is silver bromide or silver chloride.

In order to improve the reproducibility of the method, to reduce the variability of iodide uptake from wire to wire and in order for substantially all of the radioactive iodide to exchange onto the surface of the support, the support and the reaction medium should be agitated. Preferably, the agitation takes the form of rotation of the reaction vessel as opposed to direct internal stirring of the reaction medium, such that the supports "tumble" or roll in the reaction medium with each rotation.

For example, if the reaction vessel comprises a sealed individual vial, the vial may be rotated about a vertical axis or vertically end over end such that the contents tumble from end to end of the vial with each rotation. Rotation at a speed of 20 to 60 rpm is suitable, preferably below 50 rpm, more preferably below 45 rpm and most preferably about 30 rpm.

Preferably, the reaction vessel may be rotated at an angle to the horizontal such that the substrate rolls over in the reaction medium on each rotation. An angle of approximately 5° to 30° is suitable, with angles of 10° to 20° being preferred.

Suitable agitation of the reaction mixture also helps to ensure that maximum iodide uptake occurs, and that the uptake is uniform over the entire surface of the support. An advantage of the method of the invention is that it reduces the variability of iodide uptake from wire to wire when individual wires are substantially identically processed.

Suitable agitation conditions based on the above teaching may be found experimentally using routine trial and error. The agitation should not be so violent that the radioactive iodide is mechanically removed from the surface of the support. For the same reason, mechanical stirring by means of a stirrer inserted into the reaction vessel is also not advisable.

It is postulated that if two supports come into contact with each other during the ion exchange step, then the iodide salt has a tendency to be mechanically removed from the surface of the support, so leading to a lower than expected level of radioactivity for each substrate. This may provide a mechanism whereby processing multiple supports together leads to a statistical mixture of activities, i.e. uptake with an unacceptably high standard deviation from support to support. The desired method of the invention seeks to minimise contact between the radioactive coating and any other support or surface, which may lead to loss of iodide from the support.

The method may, for example, be carried out simultaneously on a number of supports by utilising a number of individual wells on a reaction plate, for example a multiwell titre plate, each well holding a single support. Alternatively, each support may be processed in an individual vial, for example a 1 ml vial. Aliquots of the reagents can then be introduced into each reaction well or vial. For safety reasons, each reaction vessel is preferably capped or closed in some way during the ion exchange reaction.

Preferably, a sufficient amount of radioactive iodide is used in the ion exchange step to produce sources with activity levels in the range of about 8880 to about 37,000 MBq (about 240 mCi to about 1 Curie). Such sources may, for example, be incorporated into radioactive bodies for use in brachytherapy which have an activity of about 7400 to about 33,300 MBq (about 200 mCi to about 900 mCi).

Given the high levels of radioactivity desired for each source, the "hot" or radioactive iodide is preferably not diluted with any "cold" (i.e. non-radioactive) iodide during the reaction i.e. the iodide is used carrier-free.

Given suitable agitation conditions, the iodide exchange step may be completed in approximately 2 to 4 hours. A reaction time of only about 2 hours enables a radioactive seed comprising a source prepared according to the method of the invention to be manufactured during a single shift of the manufacturing team. Reaction times of 4 hours or above mean that manufacture of a seed cannot be completed in a single shift.

If the radioisotopes are metal isotopes, for example palladium-103, dysprosium-159, samarium-145, cadmium-109 or ytterbium-169, they may be electroplated or ion implanted onto a metal, carbon or other conductive support using methods known in the art.

The radioactive bodies (seeds) of the invention can be delivered to the treatment site in vivo using conventional catheter based techniques which are well known in the art. Typically, a guide wire is first inserted into the patient's body, for example through an artery in the patient's thigh, as far as the site requiring treatment and then a catheter is inserted. The catheter may be threaded over the guide wire or the guide wire may pass through a hole or port at the tip of the catheter so that the catheter can threaded along the wire. Such catheters are well known in the art. Similarly catheters without guide wires may be used as may be elongate flexible probes which may or may not be hollow and which carry the radioactive body or a train of such bodies at or near their distal end.

Desirably, the catheter is shielded along all or part of its length proximal to the position at which the seeds will be positioned for radiotherapy in order to limit unnecessary exposure of healthy tissue within the patient to radiation. For example, the catheter may be formed of plastic doped with iodine or a suitable heavy metal such as, for example, lead or tungsten, which is capable of absorbing at least some of the radiation emitted by the radioactive bodies during their passage through the catheter to the treatment site. Such catheters will comprise an undoped area or treatment window at or near to the distal end. The undoped area of the catheter is positioned at the treatment site to allow radiation emitted from the radioactive bodies, when inserted inside the catheter, to reach the treatment site. Such a catheter forms a further aspect of the invention.

A shielded catheter or a catheter which is at least partially doped with a heavy metal or other radiopaque material will also have the advantage that it is visible under X-rays, which may assist in accurate placement of the catheter within a patient's body.

Typically, the seeds are mounted at the distal end of a thrust or control wire. For example, the seeds may be arranged in a linear array and encapsulated in a closed catheter insert tip which is attached to a thrust or drive wire. The catheter insert tip may comprise a flexible length of tubing preferably made of a synthetic polymer or plastic. The material of the catheter insert tip is preferably a radiation-resistant polymer as described above and preferably also sufficiently transparent that the location of the radioactive seeds is visible. The catheter insert tip is preferably assembled by first attachment of one end of the flexible tubing to the thrust or drive wire, giving a wire with an empty open-ended tip assembly attached at the distal end, and concurrently sealing one end of the tubing attachment. The radioactive seeds, with optional spacers or articulators, are then loaded into the open tubing, and the open end sealed to give the desired sealed catheter insert tip.

The attachment of the flexible tubing of the catheter insert tip to the thrust or drive wire can be achieved by thermal welding using a heat-shrunk material, especially a plastic, or by crimping on using e.g a tightened O-ring or by using a medical grade adhesive such as an epoxy or cyanoacrylate. Preferably any adhesive used is radiation-resistant. The thrust or drive wire may advantageously be shaped at the attachment end to receive the flexible tubing in a secure fit, e.g. be of slightly larger diameter at the tip to resist separation once the tubing is in place over the wire.

The sealing of the catheter can be achieved by any of the above methods, plus possibly by use of a plug or stopper arrangement fixed in position. Whatever method is used, it is important that the distal end of the catheter insert tip is free from rough edges, e.g. is rounded, so that it can freely navigate through an outer catheter without undue friction or resistance.

The wire is then fed into the proximal end of a catheter tube, the closed distal end of which has already been inserted inside the patient at least as far as the site to be treated. Part of the thrust or drive wire remains outside the patient's body at all times so that the positioning of the seeds may be adjusted, for example during or following X-ray fluoroscopy, and so that the seeds may be readily removed by retracting the wire.

Immediately following PTCA or PTA, a closed catheter may be inserted into a patient's coronary artery to a point distal to the treatment site and then the seeds are inserted as far as the treatment site for radiotherapy. Alternatively, the same catheter may be used first for PTCA or PTA treatment with, following deflation of the balloon, the insertion of a thrust or control wire bearing the radioactive seeds. The wire bearing the radioactive seeds can also be inserted into the catheter whilst the angioplasty balloon is still inflated. The closed catheter used for the PCTA is generally supplied sterile and is disposable. The thrust or guide wire bearing the radioactive seeds is used within this closed outer catheter, and hence is never in direct contact with the patient's bodily fluids. Consequently the wire bearing the radioactive seeds does not itself need to be sterile and can be reused in further patients with suitable cleansing and dose recalibration as necessary.

The movement of the seeds may also be controlled using hydraulic pressure. Such a system is disclosed in U.S. Pat. No. 5,683,345. Alternatively, as mentioned above, the radioactive body or probe may be mounted in a distal portion of a catheter and positioned and withdrawn by movement of the catheter or probe as a whole. Such a system is described by Dake in U.S. Pat. No. 5,199,939.

The seeds of the invention may also be used to treat a patient with a stent already in place in the artery.

The radioactive bodies of the invention may be used as temporary implants for the treatment of cancers, for example head and neck cancers, melanoma, brain cancers, non-small cell lung cancer, and ovarian, uterine and cervical cancer and other diseases including proliferative diseases, arthritis, urethral stricture and fibroid uterine tumours. Due to their high levels of radioactivity, it is unlikely that the bodies will be useful for permanent implantation brachytherapy. The bodies may also be useful in the prevention of restenosis following PTCA or PTA.

As a further aspect of the invention there is provided a method of treatment of a condition which is responsive to radiation therapy, for example cancer and especially restenosis, which comprises the temporary placement of a low energy X-ray emitting source, for example iodine-125, having an activity in the range 2000 to about 129,500 MBq (56 mCi to about 3.5 Ci), preferably about 3700 to 37,000 MBq (about 100–1000 mCi), most preferably 7400–18,500 MBq (200–500 mCi) and especially preferably 9250–14,800 MBq (250–400 mCi), at the site to be treated within a patient for a sufficient period of time to deliver a therapeutically effective dose.

Preferably, the method of treatment of the invention is employed to inhibit restenosis at a site within the vascular system of a patient which has previously been subjected to PTCA or PTA.

Embodiments of the invention will be further illustrated by reference to the following non-limiting Examples and to the accompanying drawings, in which.

Figure 1:
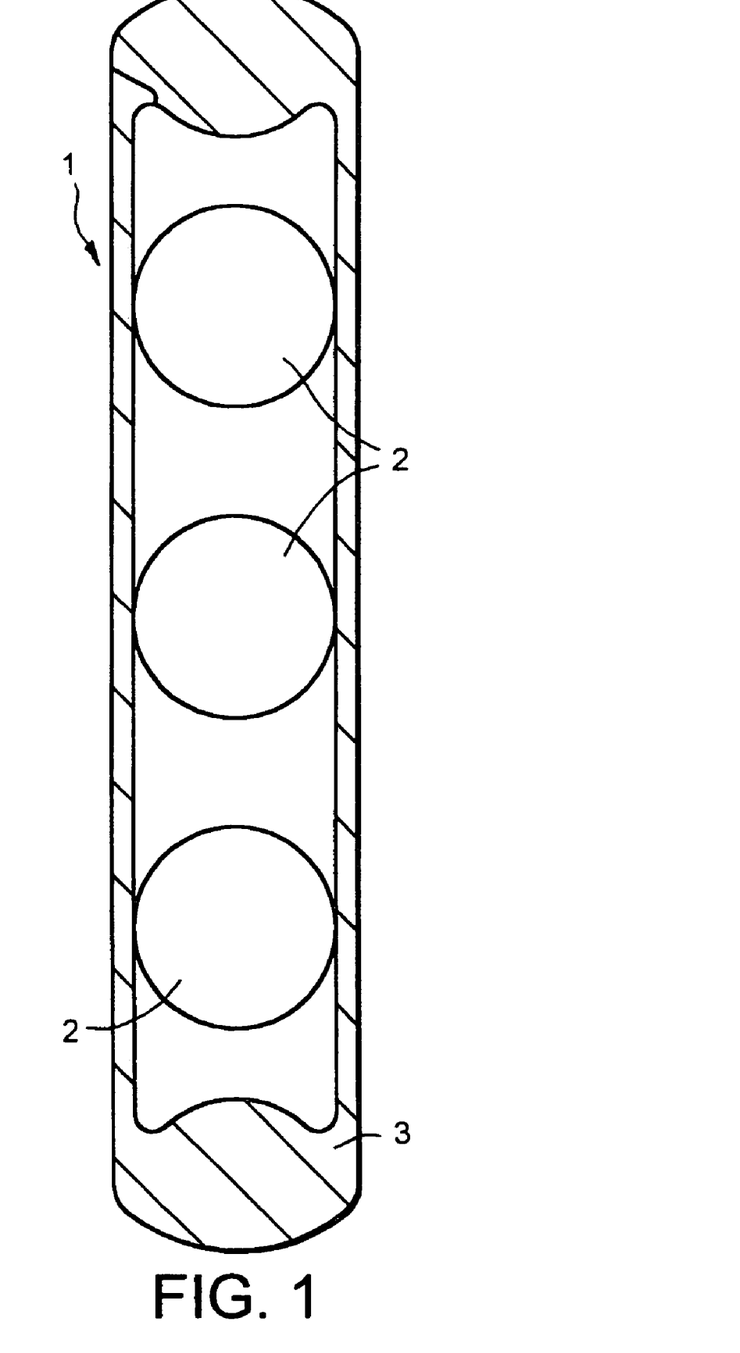
FIG. 1 is a drawing of a seed according to the invention.

FIG. 1 illustrates a seed 1 comprising three ion exchange resin beads 2 onto which a radionuclide, for example iodine-125, has been adsorbed, inside a metal container 3, for example made of titanium.

Figure 2:
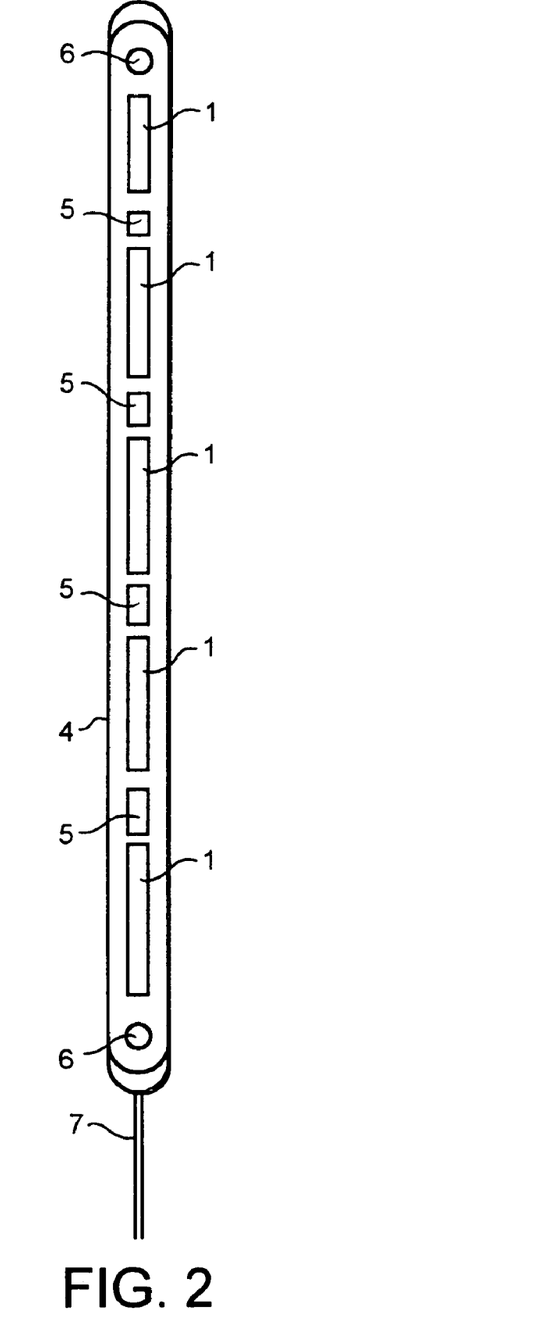
FIG. 2 is a drawing of a series of seeds mounted on a catheter insert wire.

FIG. 2 illustrates a train of seeds 1 ready for insertion into a catheter. The seeds are encapsulated in a polymer material 4 and separated by articulators 5, also made of polymer material. Markers 6 made of a radiopaque material are present at each end of the seed train to facilitate placement of the train inside a patient's body. The encapsulated seeds are attached to a thrust wire 7 which is manipulated to position the train inside the patient.

Figure 3:
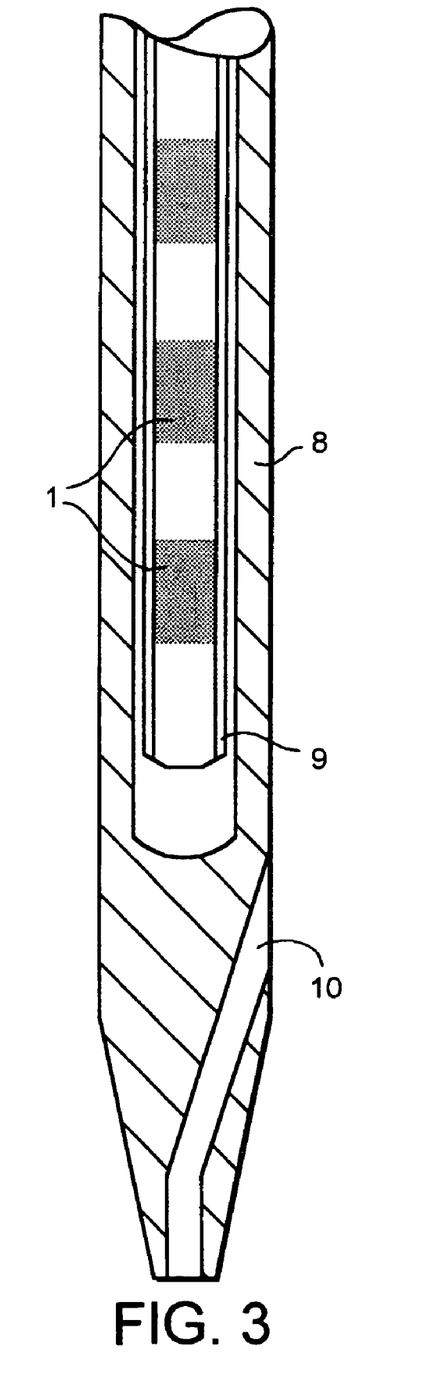
FIG. 3 is a drawing of a catheter insert tip showing encapsulation of a number of seeds and the insertion of the tip inside another catheter.

FIG. 3 illustrates the distal end of a catheter 8 loaded with radioactive seeds 1. The seeds are encapsulated in a catheter insert tip 9 which is inserted inside the lumen of the catheter 8. The catheter 8 is provided with a port 10 through which a guide wire passes when the catheter is being inserted into the patient.

EXAMPLES

Materials for Examples 1 and 2

AG1-X8 ion exchange resin (Bio-Rad) sieved to approx. 500–600 μm diameter.

Example 1

The iodide solution used in this example had an activity of 902 mCi/ml and a total volume of 1.33 cm³, giving a total activity of 1090 mCi. The supernatant assay was 162.7 mCi. The target activity was 80 mCi per bead.

The desired number of resin beads are placed in a bottle and soaked with 1 M NaCl solution for between 30 minutes and 2 hours. The supernatant is removed and the resin is washed twice with water. The iodide solution is added to the resin and the mixture is stirred for between 4 and 72 hours. The stirrer bar and supernatant are removed and the resin is dried on a heating block. The activity on each individual bead is then counted.

Figure 4:
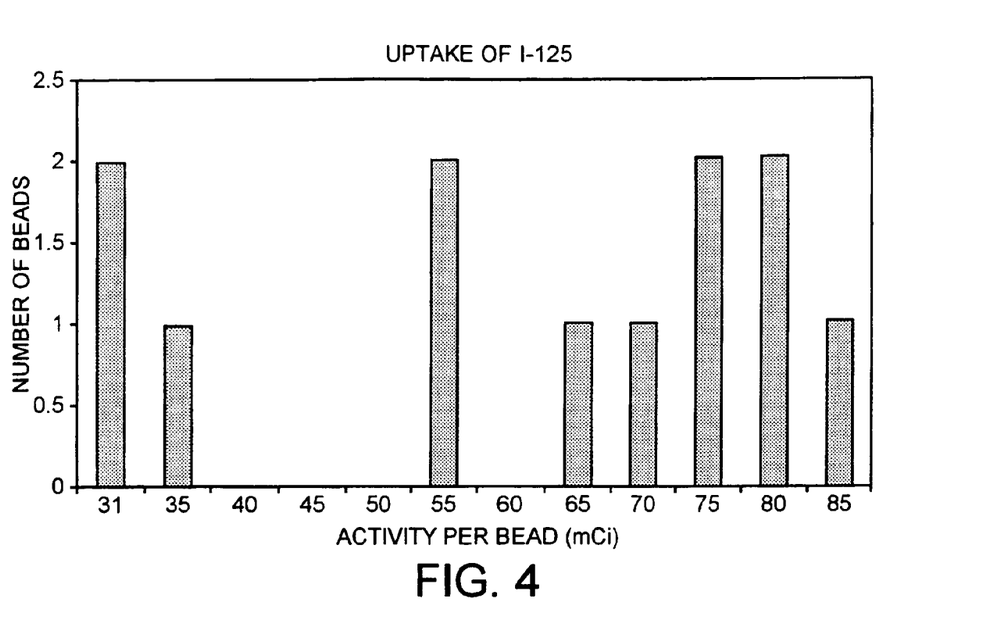
FIGS. 4 and 5 are plots of activity distribution following uptake of iodine-125 by ion exchange resin beads.

The activity distribution is plotted in FIG. 4.

Example 2

The iodide solution used in this example consisted of inactive sodium iodide at $3.9 \times 10^{-4}$ M containing Na $^{125}$I at about 20 kBq/ml. This gives the same amount of iodide per bead as 70 mCi $^{125}$I at a standard specific activity.

Resin beads are soaked in 1 M NaCl (2 ml) for 40 minutes. The supernatant is filtered off and the resin is washed with AnalaR water until the washings are free from chloride as shown by testing with silver nitrate solution. The resin is dried on a heating block and each bead is individually placed into a separate well of a 96 well plate. Iodide solution (200 μl) is added to each bead. The lid is placed on the plate and sealed with clingfilm to reduce evaporation. The plate is allowed to stand for between 24 and 72 hours. The supernatants are removed and each bead is rinsed with 200 μl AnalaR water which is also removed. Finally the beads are dried on a heating block and the activity of each is measured.

Figure 5:
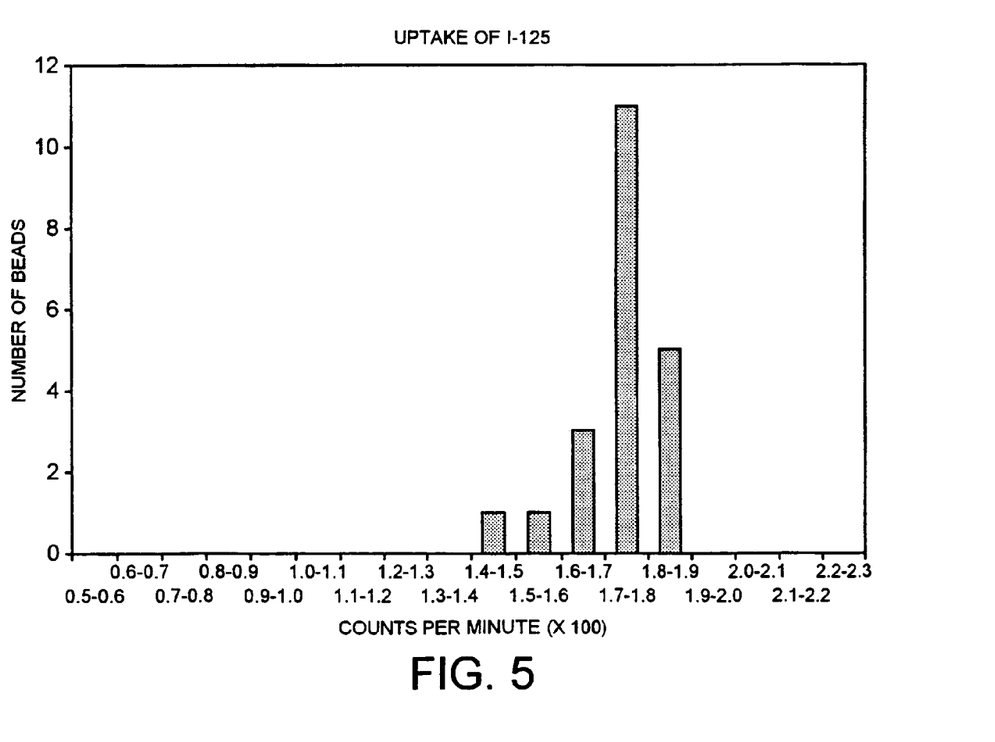

The activity distribution is plotted in FIG. 5.

The beads prepared according to Examples 1 or 2 are loaded into titanium capsules which are sealed, e.g. by welding, to form seeds. Typically such capsules are 4.5 mm×0.8 mm external dimension titanium cylinders welded shut at one end before bead loading and laser welded shut at the other after loading. Generally 3 or 4 iodine labelled beads and 2 or 3 similarly sized lead or silver spacers are loaded into each capsule.

Example 3

A 10 to 30 percent solution of methacrylamide, methylene bisacrylamide, and N,N,N-trimethyl-3-[(2-methyl-1-oxo-2-propenyl)amino]-1-propanaminium chloride in water is sparged with nitrogen and thermally polymerized in the presence of sodium bisulphite and sodium persulfate. Excess water is removed and the cross-linked resin is dried, ground and sieved to provide beads of uniform particle size distribution. Each bead is then individually treated with a concentrated solution of sodium 125-iodide and sodium hydroxide in water in the presence of intermittent ultrasonication until the bead resin swells sufficiently to absorb the surrounding water and salts. The swollen beads containing iodide-125 are then dried in a warm flow of nitrogen. The resulting polymer resin beads are placed in a titanium can and sealed. The number of beads per can depends on the amount of radioactivity desired to be incorporated in each bead and each can.

Example 4

A 10 to 15% solution of methacrylamide, methylene bisacrylamide, and N,N,N-trimethyl-3-[(2-methyl-1-oxo-2-propenyl)amino]-1-propanaminium chloride in water containing 2,2'-azobis(2-methylpropionamidine) dihydrochloride is sparged with nitrogen, dispersed in an equal volume of oxygen-free toluene with stirring and thermally polymerized overnight. The organic solvent is removed by steam distillation and excess water is removed azeotropically. The remaining bead resin is dried and sieved to provide a uniform particle size distribution. Each bead is then individually treated with a concentrated solution of sodium 125-iodide and sodium hydroxide in water in the presence of intermittent ultrasonication until the bead resin swells sufficiently to absorb the surrounding water and salts. The swollen beads containing the iodide-125 are then dried in a warm flow of nitrogen. The resulting polymer resin beads are placed in a titanium can and sealed. The number of beads per can depends on the amount of radioactivity desired to be incorporated in each bead and each can.

Example 5

A polymer bead resin is prepared from divinyl benzene, styrene and vinyl benzyl chloride by free radical polymerization under limited coalescence polymerization conditions. The resin is then treated with 4-amino-2,2,6,6-tetramethylpiperidine and then with trimethylamine in DMF. Solvent and excess amines are removed by washing with aqueous acetone and then water. The resin is dried, sieved to uniform particle size, and treated with a solution of sodium 125-iodide and sodium hydroxide in water and dried. The resulting polymer resin is resistant to degradation by radiation prior to sealing in, for example, a titanium or other casing to form a seed.

Example 6

Preparation of High Activity Wires Using a 48 Well Titre Plate

AgBr-coated silver wires were prepared from clean 3 mm long silver wires having 0.5 mm diameters by first treating with nitric acid for 2 minutes followed by treating with a mixture of HCl and sodium chlorite to form a layer of silver chloride on the wires. The wires were rinsed and then treated with a solution of sodium bromide to form silver bromide coated wires. This treatment was repeated to ensure complete formation of silver bromide on the wire surface. The coated wires were then placed one each into 12 wells of a 48 well titre plate (Falcon 3230 multiwell tissue culture plate, 48 well, flat bottom with low evaporation lid, sterile gamma irradiated, Becton Dickinson). Enough sodium iodide solution was added to each well to provide 50 µg of iodide per well. In this case, this came to a volume of 800 µl. The plate was then capped and gently rocked back and forth using an Orbitron Rotator II (model 260250) from Boekel Scientific) to agitate the wires within the wells. After 6 hr, the wires were gently removed and analysed by UV spectrophotometry for adsorbed iodide. The results are shown below:

| Well/wire # | µg I (wire) | Activity/wire** | % Iodide remaining in solution |
|---|---|---|---|
| 1 | 48.989 | 832.813 | 1.38 |
| 2 | 50.312 | 855.304 | 1.15 |
| 3 | 48.693 | 827.781 | 1.89 |
| 4 | 46.745 | 794.665 | 1.22 |
| 5 | 49.604 | 843.268 | 1.35 |
| 6 | 50.061 | 851.037 | 1.33 |
| 7 | 48.675 | 827.475 | 1.31 |
| 8 | 51.25 | 871.25 | 0.97 |
| 9 | 46.744 | 794.648 | 1.21 |
| 10 | 49.762 | 845.954 | 1.06 |
| 11 | 49.767 | 846.039 | 1.21 |
| 12 | 48.444 | 823.548 | 1.16 |

-continued

| Well/wire # | µg I (wire) | Activity/wire** | % Iodide remaining in solution |
|---|---|---|---|
| Average | 49.09 | 834.48 | 1.27 |
| % RSD | 2.75 | 2.75 | |

RSD = relative standard deviation
**= calculated

Thus, with a minimum of effort, 12 wires were prepared with elevated levels of iodide adsorbed. Assuming a specific activity of 17 Curies/mg sodium iodide, these wires would exhibit an average activity of 834.48 millicuries each and are suitable for subsequent placement into titanium tubes and welding to prepare radioactive iodine seeds.

Example 7

Study of the Impact of Different Angles on the Uptake of Iodide in a Titre Plate Wires were treated as in Example 6 using different angles of rotation.

The rotator used in this study was a custom made rotator built such that the speed of rotation was fixed at 30 rpm and the angle of the rotating barrel was 30 degrees to the horizontal. In test run A, this rotator was propped up such that the barrel pointed almost directly perpendicular to the bench top (i.e. to horizontal). Thus, when a titre plate was affixed to the barrel, it (being 90 degrees to the barrel) rotated in a fairly horizontal plane (i.e. within 10 degrees from horizontal). The titre plate used was a FALCON®, 3230 MULTIWELL™ Tissue Culture plate from Becton Dickinson. The bottom of the plate was adhesively fixed to the end of the rotator by "gluing" it to a plastic insert in the barrel with acetone.

The data shown below demonstrate the reproducibility of this process with a relative standard deviation of 4.3%.

| A. Wire # | Wire (µg I) | % Iodide remaining in solution |
|---|---|---|
| Starting 50 µg I | | |
| 1 | 38.388 | 1.50 |
| 2 | 37.876 | 1.41 |
| 3 | 38.919 | 1.35 |
| 4 | 39.545 | 1.37 |
| 5 | 37.172 | 1.50 |
| 6 | 37.822 | 1.39 |
| 7 | 39.47 | 1.29 |
| 8 | 39.842 | 1.33 |
| 9 | 42.142 | 1.63 |
| 10 | 38.547 | 1.34 |
| 11 | 35.568 | 1.46 |
| 12 | lost wire | 1.24 |
| Average | 38.663 | 1.21 |
| Std Dev | 1.679 | 0.09 |
| Dev % | 4.344 | |
| % coverage | 77.33 | |

Std Dev = standard deviation, Dev = deviation

In run B, the rotator was placed in its normal position (i.e. 30 degrees to horizontal) such that when the plate was affixed perpendicularly to the barrel (being at 90 degrees to the barrel), the plate was in a plane at a 60 degree angle relative to the horizontal. The reaction wells in the plate were able to hold the fluid inside and the wires were seen to slide along the seam formed from the bottom of the well and the wall of the well until they fell completely across the well and started this motion again.

The results shown below again demonstrate very good uptake of iodide onto the individual wires.

| B. Wire # | Wire ($\mu$g I) | % Remaining |
|---|---|---|
| Starting 50 $\mu$g I | | |
| 1 | 50.824 | 1.91 |
| 2 | 52.513 | 1.58 |
| 3 | 51.171 | 2.15 |
| 4 | 50.824 | 1.91 |
| 5 | 51.256 | 1.71 |
| 6 | 50.627 | 1.77 |
| 7 | 52.329 | 1.47 |
| 8 | 51.99 | 1.99 |
| 9 | 51.678 | 1.75 |
| 10 | 50.911 | 1.63 |
| 11 | 52.305 | 1.62 |
| 12 | 51.07 | 2.68 |
| 13 | 51.777 | 1.85 |
| 14 | 50.785 | 1.72 |
| 15 | 36.392 | 33.10 |
| 16 | 50.899 | 2.09 |
| Average | 50.46 | 3.81 |
| Std Dev | 3.80 | 7.82 |
| Dev % | 7.54 | |
| % coverage | 100.92 | |

In both cases, 800 $\mu$l of sodium iodide dissolved in sodium hydroxide was placed into each well along with a single AgBr coated silver wire. The rotation speed was fixed at 30 rpm. Reaction time was taken to be 6 hours. Assuming a specific activity of 17 Curies/mg of sodium iodide, these wires would adsorb 857.6 milli Curies on average.

Example 8

Kinetics of Iodide Uptake by AgBr Coated Ag Wires

Wires were prepared as in Example 6 using 800 $\mu$l of sodium iodide/sodium hydroxide per well and one AgBr coated silver wire per well of a 48 well titre plate. The target concentration of iodide per wire was 50 $\mu$g. Six wells were sampled at varying times to assess the kinetics of iodide uptake. The results suggest that 4 hrs is sufficient for complete uptake although the variability of iodide per wire improves with time of reaction.

| 4 hrs. | Iodide $\mu$g/wire | 5 hrs. | Iodide $\mu$g/wire | 6 hrs. | Iodide $\mu$g/wire | 7 hrs. | Iodide $\mu$g/wire |
|---|---|---|---|---|---|---|---|
| 1 | 50.74 | 7 | 52.85 | 13 | 51.94 | 19 | 53.73 |
| 2 | 52.27 | 8 | 56.72 | 14 | 51.36 | 20 | 52.29 |
| 3 | 59.58 | 9 | 52.88 | 15 | 51.63 | 21 | 53.77 |
| 4 | 50.43 | 10 | 51.90 | 16 | 52.70 | 22 | 52.28 |
| 5 | 52.12 | 11 | 52.48 | 17 | 52.71 | 23 | 53.01 |
| 6 | 51.18 | 12 | 50.85 | 18 | 52.42 | 24 | 52.74 |
| average | 52.72 | | 52.95 | | 52.12 | | 52.97 |
| Std Dev | 3.44 | | 2.00 | | 0.57 | | 0.67 |

| 4 hrs. | Iodide $\mu$g/wire | 5 hrs. | Iodide $\mu$g/wire | 6 hrs. | Iodide $\mu$g/wire | 7 hrs. | Iodide $\mu$g/wire |
|---|---|---|---|---|---|---|---|
| Dev % | 6.52 | | 3.77 | | 1.09 | | 1.26 |
| % coverage | 105.44 | | 105.90 | | 104.25 | | 105.94 |

Example 9

This example used AgBr coated silver wires as used in the production of model 6711 seeds.

One wire was placed into each of four ½ dram glass vials and 800 $\mu$l of sodium [$^{125}$I] iodide solution (700 mCi, 25.9 GBq)) was added. The lidded vials were placed into a copper tube of internal diameter 13 mm and length 162 mm closed at one end. The tube was inserted closed end first into a device which was capable of rotating the tube around its axis at a rate of 45 rpm at an angle 30° from the horizontal (open end upwards). This rotation had the effect of rolling the silver wire in the iodide solution. The tube was rotated for a period of 2 hours after which a 50 $\mu$L sample was taken from the supernatant and counted to check for iodide uptake onto the wires. As all measurements indicated less than 10% iodide remained in solution, the supernatant was removed and the wires were loaded into titanium cans which were welded and leak tested using the standard methods. A second batch of four high-activity seeds was prepared in a similar manner. The apparent activity of each seed was measured and is listed in Table 1.

TABLE 1

| Apparent activity measured | |
|---|---|
| Seed number | Apparent Activity/mCi |
| 1 | 323 |
| 2 | 399 |
| 3 | 426 |
| 4 | 412 |
| 5 | 387 |
| 6 | 383 |
| 7 | 359 |
| 8 | 392 |

The apparent activity of the seeds is less than the activity taken up by the wire due to absorption of the $^{125}$I X-rays by the silver wire and the titanium capsule. The ratio of actual to apparent activity is known to be about 1.6 for model 6711 $^{125}$I seeds.

Example 10

(a) One Step Method for the Preparation of Ag/AgBr/AgI Wires 1500 cleaned silver wire substrates in a 30 ml square vial were treated with 14 ml of a solution containing 3 M NaCl, NaBr (200 $\mu$g/wire) and NaI (3 $\mu$g/wire). To this was added 1 ml of water containing 309 mg of potassium ferricyanide. The vial was then rotated for 4 hours. The silver bromide coated wires produced also contained a small amount of iodide (~3 $\mu$g) in addition to the bromide.

It was found empirically that a greater quantity of AgBr can be formed on a silver wire substrate and at a faster rate if a small amount of NaI is added to an oxidizing mixture comprising sodium bromide and potassium ferricyanide.

(b) Method for Exchange of Bromide for Iodide

Twenty wires prepared according to Example 10(a) were individually placed in separate wells of a 48 well plate, the bottom of which was affixed perpendicularly to a rotator. Each well in which a wire was placed also contained 800 µl of a solution comprising 50 µg of NaI. The plate was then rotated in the plane of the plate at an angle of about 20 degrees from the horizontal for 4 hours.

Average iodide uptake: 53.2 µg I/wire
Std. Dev.: 0.78
% Dev. 1.5%

What is claimed is:

1. A radioactive body suitable for temporary or permanent implantation in a mammal for use in brachytherapy containing a low energy X-ray emitter which emits low energy X-rays at an activity equivalent to iodine-125 in the range of about 74 to 185 GBq (about 2 Ci to 5 Ci).

2. A radioactive body as claimed in claim 1 wherein the low energy X-ray emitter is iodine-125, palladium-103, dysprosium-159, samarium-145, cadmium-109 or ytterbium-169.

3. A radioactive body as claimed in claim 1 wherein the low energy X-ray emitter is iodine-125 or palladium-103.

4. A radioactive body as claimed in claim 1 which is a sealed source.

5. A radioactive body as claimed in claim 1 which is a seed.

6. A radioactive body as claimed in claim 1 which comprises one or more radioactive sources.

7. A radioactive body as claimed in claim 6 wherein the radioactive source comprises a radioisotope and one or more supports.

8. A radioactive body as claimed in claim 7 wherein the support is a bead, rod, wire or filament.

9. A radioactive body as claimed in claim 7 wherein the support is a bead of ion exchange resin, graphite, ceramic, zeolite, any form of carbon or another porous material.

10. A radioactive body as claimed in claim 1 wherein the X-ray emitter is iodine-125, and wherein the iodine-125 is present in the form of an insoluble metal iodide on the surface of a suitable support.

11. A radioactive body as claimed in claim 10 wherein the support comprises a metal chosen from silver, copper, palladium, thallium, gold, lead or platinum.

12. A radioactive source as claimed in claim 10 wherein the metal is silver.

13. A radioactive body as claimed in claim 1, which is cylindrical and which contains a plurality of radioactive sources, wherein each source comprises a radioisotope and a support in the shape of a bead, rod, wire or filament, characterised in that the sources at the ends of the cylindrical body have higher activity than the sources at the centre of the cylindrical body, such that the radiation field around the radioactive body is substantially cylindrically uniform.

14. A radioactive body as claimed in claim 13 which comprises four sources, each source comprising a solid support in the shape of a bead or rod, and wherein the central two supports have lower activity than the end two supports.

15. A radioactive body as claimed in claim 14 wherein the low energy X-ray emitter is iodine-125 and the ratio of activities of the sources is 10:8:8:10.

16. A radioactive body as claimed in claim 14 wherein the low energy X-ray emitter is palladium-103 and the ratio of activities of the sources is 10:9:9:10.

17. A radioactive body as claimed in claim 13 wherein each support comprises ion exchange resin, graphite, ceramic, zeolite, any form of carbon or another porous material.

18. A radioactive body as claimed in claim 13 wherein the X ray emitter is iodine-125, and wherein the iodine-125 is present in the form of an insoluble metal iodide on the surface of a support.

19. A radioactive body as claimed in claim 18 wherein the support comprises a metal chosen from silver, copper, palladium, thallium, gold, lead or platinum.

20. A radioactive body as claimed in claim 19 wherein the metal is silver.

21. An elongate radioactive body containing a plurality of radioactive sources of different activities, wherein each of said plurality of radioactive sources comprises a radioactive support, such that there is a substantially cylindrically uniform radiation field around the body, wherein the radioactive sources are either radiometals or insoluble salts thereof.

22. A radioactive source comprising a radioisotope and a support in the form of a bead with an activity of about 74 to 185 GBq, wherein the radioactive sources are either radiometals or insoluble salts thereof.

23. A method of treatment of a condition which is responsive to radiation therapy, which comprises the temporary placement of a low energy X-ray emitting source which emits low energy X-rays at an activity equivalent to iodine-125 in the range of about 74 to 185 GBq at the site to be treated within a patient for a sufficient period of time to deliver a therapeutically effective dose, wherein the low energy X-ray source is either a radiometal or insoluble salts thereof.

24. A method as claimed in claim 23 wherein the condition to be treated is cancer, a proliferative disease, arthritis, urethral stricture, fibroid uterine tumours or restenosis of coronary or peripheral arteries.

25. A method as claimed in claim 23 to inhibit restenosis at a site within the vascular system of a patient which has previously been subjected to PTCA or PTA.

* * * * *